United States Patent
MacDougall et al.

(10) Patent No.: US 11,666,778 B2
(45) Date of Patent: Jun. 6, 2023

(54) OPTICAL SURFACE APPLICATOR WITH INTEGRATED DIFFUSER

(71) Applicant: LUMEDA INC., Rocky Hill, CT (US)

(72) Inventors: Trevor MacDougall, South Dartmouth, MA (US); Yi Yang, Storrs, CT (US)

(73) Assignee: Lumeda Inc., Rocky Hill, CT (US)

( * ) Notice: Subject to any disclaimer, the term of this patent is extended or adjusted under 35 U.S.C. 154(b) by 0 days.

(21) Appl. No.: 17/594,162

(22) PCT Filed: Jun. 8, 2021

(86) PCT No.: PCT/US2021/036312
§ 371 (c)(1),
(2) Date: Oct. 5, 2021

(87) PCT Pub. No.: WO2022/260650
PCT Pub. Date: Dec. 15, 2022

(65) Prior Publication Data
US 2022/0387815 A1    Dec. 8, 2022

(51) Int. Cl.
*A61N 5/06*    (2006.01)

(52) U.S. Cl.
CPC ...... *A61N 5/062* (2013.01); *A61N 2005/0627* (2013.01); *A61N 2005/0664* (2013.01)

(58) Field of Classification Search
CPC ...... A61N 5/06; A61N 5/0616; A61N 5/0618; A61N 5/062; A61N 5/0621; A61N 5/0622;

(Continued)

(56) References Cited

U.S. PATENT DOCUMENTS

| | | | | |
|---|---|---|---|---|
| 5,339,223 A | * | 8/1994 | Kremenchugsky | .. D03D 15/283 385/115 |
| 6,290,713 B1 | * | 9/2001 | Russell | ........... A61N 5/0616 607/91 |

(Continued)

FOREIGN PATENT DOCUMENTS

| | | | |
|---|---|---|---|
| WO | 2010019800 A1 | 2/2010 | |
| WO | WO-2010019800 A1 * | 2/2010 | ........... A61N 5/0601 |
| WO | 2020097186 A1 | 5/2020 | |

*Primary Examiner* — Ahmed M Farah
(74) *Attorney, Agent, or Firm* — Matthew J Patterson (57) ABSTRACT

A therapeutic light delivery apparatus and method are disclosed. The apparatus includes a light source and an integrated optical applicator. The integrated optical applicator includes a plurality of light emitting devices and detector fibers fixedly spatially positioned within a flexible matrix material. The light emitting devices can be positioned a predetermined distance from an application side of the integrated optical applicator comprising an accurate and repeatable standoff position. A flexible matrix material is disclosed having a high scattering coefficient to produce a uniform irradiance pattern and predetermined fluence. A method of performing a photodynamic therapy procedure is disclosed that includes providing an integrated optical applicator couple to a therapy light source, providing a photosensitizing drug to a tissue of a patient, positioning an application side of the integrated optical applicator against a target area of the tissue, delivering a therapy light to the target area, and producing an irradiance pattern.

20 Claims, 4 Drawing Sheets

(58) Field of Classification Search
CPC ............... A61N 5/0624; A61N 5/0625; A61N 2005/063
USPC ..................................... 607/88–91; 128/898
See application file for complete search history.

(56) References Cited

U.S. PATENT DOCUMENTS

| | | | | |
|---|---|---|---|---|
| 8,585,707 | B2* | 11/2013 | Rogers | A61N 5/062 |
| | | | | 606/88 |
| 8,986,358 | B2* | 3/2015 | Svanberg | A61N 5/062 |
| | | | | 607/92 |
| 2013/0123648 | A1* | 5/2013 | Stampoulidis | A61N 5/062 |
| | | | | 600/478 |
| 2013/0304019 | A1* | 11/2013 | Cooper | A61N 5/062 |
| | | | | 604/20 |
| 2014/0276354 | A1* | 9/2014 | Piergallini | A61K 8/498 |
| | | | | 222/394 |
| 2015/0202456 | A1* | 7/2015 | Andersen | A61K 38/164 |
| | | | | 604/20 |
| 2020/0222712 | A1* | 7/2020 | Schultheis | G02B 5/0242 |
| 2022/0001193 | A1* | 1/2022 | Zhu | A61N 5/062 |

* cited by examiner

OPTICAL SURFACE APPLICATOR WITH INTEGRATED DIFFUSER

CROSS REFERENCE TO RELATED APPLICATIONS

This application claims the benefit of U.S. Provisional Patent Application Ser. No. 63/036,584 filed 9 Jun. 2020 as well as Patent Cooperation Treaty Patent Application Serial No PCT/US21/36312 filed 8 Jun. 2021. The disclosures of the applications above are incorporated herein by reference in their entirety.

BACKGROUND OF THE DISCLOSURE

Field of the Disclosure

The present disclosure relates to photodynamic therapy.

Description of the Related Art

Light therapy can be used for the treatment of conditions in multiple ways. For example, light therapies involve the delivery of a therapeutic light through a fiber optic device placed proximal to or within a target tumor.

Light therapies can be combined with prior administration of light sensitizing medication (i.e., photosensitizer) that absorbs the therapeutic light and interacts with surrounding tissue constituents (e.g., oxygen) to generate reactive species that can destroy the target tissue. This form of therapy is known as photodynamic therapy ("PDT").

Figure 1:
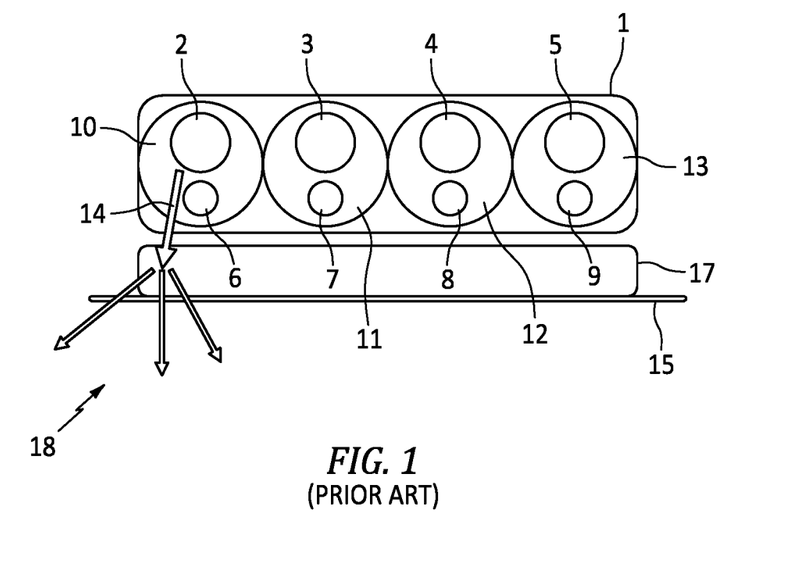
FIG. 1 is a schematic representation of a cross section of a PDT system of the prior art.

One embodiment of a prior art PDT system is shown with reference to FIG. 1 which includes an applicator flap 1 shown in cross section. Applicator flap 1 includes source emitters 2-5 and optional detector fibers 6-9. In this configuration, source emitting devices in the form of source emitters 2-5 and optional detector fibers 6-9 are positioned within channels 10-13. The number of channels and their position are predetermined by the manufacture. Some known applicator flaps include a Freiburg flap manufactured by Elekta and a H.A.M. applicator available from Mick Radio-Nuclear Instruments. In addition, the light transmissibility characteristics are similarly predetermined by the manufacturer. In certain embodiments of PDT, the emitted light 14 is not sufficiently diffused to provide the desired illumination pattern on a target area of tissue 15. Such limitations of prior art PDT systems hamper a physician's ability to deliver effective therapeutic treatment. In some prior art embodiments, a separate diffusion layer 17 is positioned between applicator flap 1 and tissue to produce a scattered light pattern 18. The addition of separate diffusion layer 17 increases the complexity of the system and could lead to possible errors at least having to do with positioning of the applicator flap.

Some prior art PDT is set forth in the paper titled "An Optical Surface Applicator for Intraoperative Photodynamic Therapy", by Sarah Chamberlain, et al, published in Lasers in Surgery and Medicine, 2019, the contents of which are incorporated herein in its entirety.

What is needed is an improved applicator flap to overcome the shortcomings of the prior art.

SUMMARY OF THE DISCLOSURE

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an optical light delivery device. The optical light delivery device may include a plurality of source emitting devices configured to be optically coupled to a source, a flexible matrix encapsulating and spatially fixing the plurality of source emitting devices therein, and the flexible matrix configured to scatter a light emitted from at least one of the plurality of source emitting devices. Other embodiments of this aspect include corresponding computer systems, apparatus, and computer programs recorded on one or more computer storage devices, each configured to perform the actions of the methods.

Implementations may include one or more of the following features. The optical light delivery device may include at least one detector fiber encapsulated and spatially fixed within the flexible matrix proximate the plurality of source emitting devices, the at least one detector fiber configured to detect a light emitted from at least one of the plurality of source emitting devices and configured to be coupled to a detector. The plurality of source emitting devices are spatially fixed at a predetermined standoff position from an application side of the optical light delivery device. the optical light delivery device where the plurality of source emitting devices are axially aligned and spatially fixed at a first predetermined spacing along a width of the flexible matrix and where the at least one detector fiber may include a plurality of detector fibers that are axially aligned and spatially fixed at a second predetermined spacing along the width of the flexible matrix. The plurality of source emitting devices may include a plurality of cylindrical light diffusers and where the plurality of cylindrical light diffusers are optically coupled to a plurality of optical fibers. The optical light delivery device where the plurality of detector fibers are optically coupled to a plurality of optical fibers. The plurality of detector fibers are optically coupled to a plurality of optical fibers. The optical light delivery device where the plurality of detector fibers comprise a plurality of isotropic probes. The plurality of source emitting devices are spatially fixed at a predetermined standoff position from an application side of the optical light delivery device. The flexible matrix is selected from a group of materials having a scattering coefficient greater than 5 cm-1. The optical light delivery device is further configured to produce a fluence at the application side. Implementations of the described techniques may include hardware, a method or process, or computer software on a computer-accessible medium.

One general aspect includes an optical light delivery system that may include a therapy light source, an integrated optical applicator that may include a plurality of source emitting devices optically coupled to the therapy light source, a flexible matrix encapsulating and spatially fixing the plurality of source emitting devices therein, and the flexible matrix may include a light scattering material and is configured to scatter a therapy light emitted from at least one of the plurality of source emitting devices. The optical light delivery system where the integrated optical applicator further may include a plurality of detector fibers encapsulated and spatially fixed within the flexible matrix proximate the plurality of source emitting devices, the plurality of detector fibers optically coupled to a detector and configured to detect a therapy light emitted from at least one of the plurality of source emitting devices. The optical light delivery system where the plurality of source emitting devices are spatially fixed at a predetermined standoff position from an application side of the integrated optical applicator. The optical light delivery system where the plurality of source emitting devices are axially aligned and spatially fixed at a first predetermined spacing along a width of the flexible matrix and where the plurality of detector fibers are axially aligned and spatially fixed at a second predetermined spacing along the width of the flexible matrix. The optical light delivery system where the plurality of source emitting devices may include a plurality of cylindrical light diffusers and where the plurality of cylindrical light diffusers are optically coupled to an optical connector. The optical light delivery system where the plurality of detector fibers may include a plurality of isotropic probes and where the plurality of isotropic probes are optically coupled to the optical connector. The optical light delivery system may include an optical tether optically coupled to the optical connector. The integrated optical applicator is configured to produce a highly uniform irradiance pattern. The optical light delivery system where the flexible matrix is selected from a group of materials having a scattering coefficient greater than 5 cm-1. the optical light delivery system where the integrated optical applicator is configured to produce a predetermined fluence at an application side. Implementations of the described techniques may include hardware, a method or process, or computer software on a computer-accessible medium.

One general aspect includes a method of manufacturing an integrated optical applicator that may include providing a mold assembly defining a cavity having a bottom, a length and a width, positioning a plurality of cylindrical light diffusers in the mold assembly axially aligned along the length, at a predetermined spacing along the width and at a predetermined distance from the bottom, positioning a plurality of detector fibers in the mold assembly proximate the plurality of cylindrical light diffusers, dispensing a curable matrix material in the cavity and encapsulating the plurality of cylindrical light diffusers and the plurality of detector fibers therein, and curing the curable matrix material into a flexible matrix and spatially fixing the plurality of cylindrical light diffusers and the plurality of detector fibers therein.

Implementations may include one or more of the following features. The method of manufacturing an integrated optical applicator where the flexible matrix is may include of a light scattering material having a scattering coefficient greater than 5 cm-1. the method of manufacturing an integrated optical applicator where the light scattering material further includes light scattering particles including any of glass microspheres, metallic particles and saline. The method of manufacturing an integrated optical applicator where a portion of the flexible matrix positioned against the bottom during the curing produces an application side of the integrated optical applicator and the predetermined distance from the bottom produces a standoff position of the plurality of cylindrical light diffusers from the application side. The method of manufacturing an integrated optical applicator where a reflective coating is applied to any of a surface of the integrated optical applicator where a reflective coating is applied to any of a surface of the integrated optical applicator except for the application side.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. Implementations may include one or more of the following features. The method of performing a photodynamic therapy procedure may include providing a therapy light source, providing an integrated optical applicator that may include a plurality of source emitting devices, a flexible matrix encapsulating and spatially fixing the plurality of source emitting devices therein, and the flexible matrix may comprise a light scattering material and is configured to scatter a therapy light emitted from at least one of the plurality of source emitting devices. The method also includes optically coupling the plurality of source emitting devices to the therapy light source, providing a photosensitizing drug to a tissue of a patient, positioning an application side of the integrated optical applicator against a target area of the tissue, delivering a therapy light from at least one of the plurality of source emitting devices to at least a portion of the target area, and producing an irradiance pattern to the at least a portion of the target area. Other embodiments of this aspect include corresponding computer systems, apparatus, and computer programs recorded on one or more computer storage devices, each configured to perform the actions of the methods.

Implementations may include one or more of the following features. The method of performing a photodynamic therapy procedure may include obtaining a digital file of the target area including a position of the target area, and where the positioning of the application side of the integrated optical applicator against the target area of the tissue is based on the digital file. The method of performing a photodynamic therapy procedure may include a treatment plan, the integrated optical applicator may include spatial fixing a plurality of detector fibers proximate the plurality of source emitting devices and optically coupling the plurality of detector fibers to a detector, providing a microprocessor electronically coupled to the detector and the therapy light source, detecting the therapy light with the at least one of the plurality of detector fibers and, using the microprocessor, producing a dosage therapy light amount, and comparing, using the microprocessor, the dosage therapy light amount with the treatment plan. The method of performing a photodynamic therapy procedure may include continuing to delivering the therapy light and detecting the therapy light until the dosage therapy light amount is substantially equal to the treatment plan. Producing the irradiance pattern to the at least a portion of the target area may include producing a substantially equal fluence across the at least a portion of the target area. The method of performing a photodynamic therapy procedure where producing a dosage therapy light amount is performed on a cumulative basis during the photodynamic therapy procedure. Implementations of the described techniques may include hardware, a method or process, or computer software on a computer-accessible medium.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

The present disclosure relates to an integrated optical light therapy system which is configured to emit a diffused and controllable irradiance pattern. Such a system is useful in the treatment of cancerous tumors as well as residual abnormal tissue following surgical resection of a tumor. The present disclosure also includes methods for integrating various optical components into a light scattering material having high scattering coefficient to effectively scatter the therapy light and to produce a highly uniform irradiance pattern. In one aspect, the disclosure provides a method for spatially distributing the therapy light over a target area of a patient.

Figure 2:
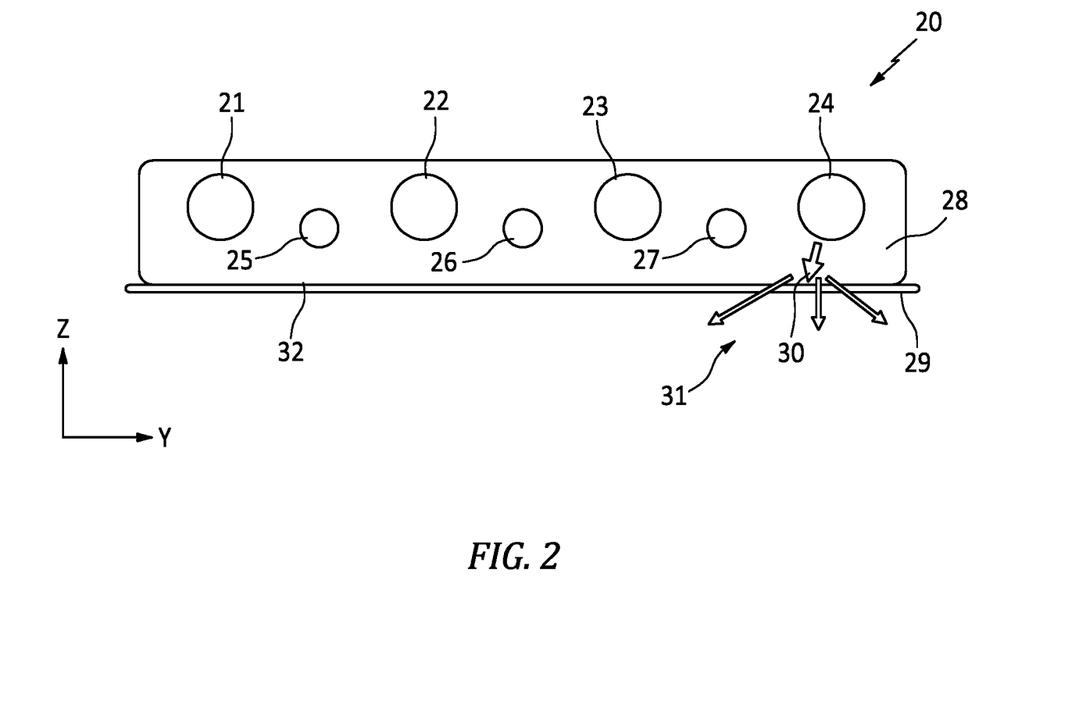
FIG. 2 is a cross section end view taken substantially along line 3-3 of FIG. 3 showing an integrated optical applicator in accordance with the present disclosure.
Figure 3:
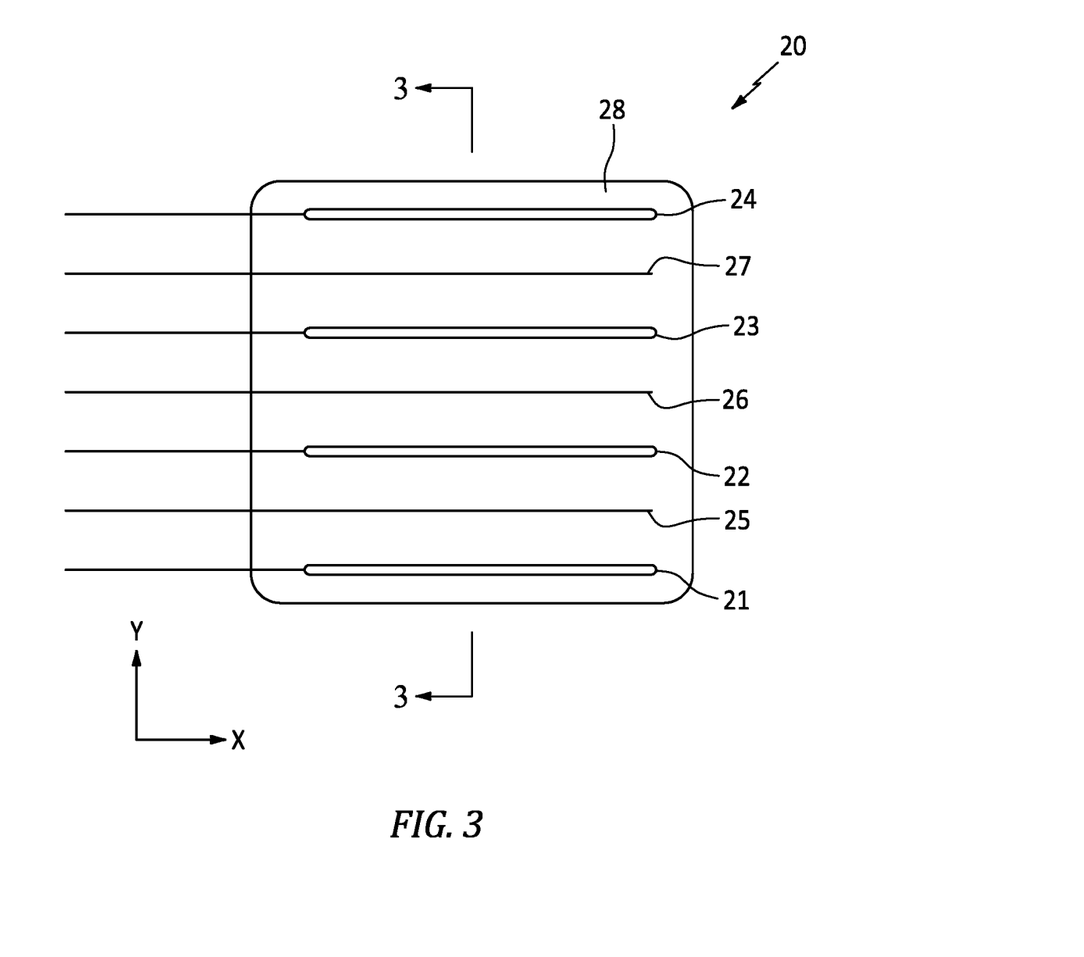
FIG. 3 is a top plan view showing an integrated optical applicator in accordance with the present disclosure.

Referring to FIG. 2, there is shown a cross sectional schematic (taken along line 3-3 in FIG. 3) of optical light delivery device in the form of an integrated optical applicator 20 in accordance with the present disclosure. Integrated optical applicator includes source emitters 21-24 and detector fibers 25-27 embedded within matrix material 28. Although a specific number of source emitters and detectors are shown, this is but an example embodiment and more or fewer of such components can be selected without departing from the scope of the present disclosure. With further reference to FIG. 3, source emitters 21-24 and detector fibers 25-27 embedded within matrix material 28 in a parallel fashion with respect to their length. Source emitters 21-24 can comprise cylindrical light diffusers which are optically coupled to a plurality of optical fibers and selectively optically coupled to a therapy light source via an optical connector (53, FIG. 6). The cylindrical light diffusers are configured to transmit light from the light source at a predetermined wavelength (nm) and substantially equal fluence (J/cm$^2$) to deliver a dosage of therapy light to a target area of a tissue 29. One embodiment of a suitable cylindrical light diffuser is model RD-50 available from Rakuten Medical. The position of source emitters 21-24 is spatially fixed within integrated optical applicator 20 in the X, Y and Z directions wherein X is a position along a length of the optical applicator, Y is a position along a width of the optical applicator and Z is a position along a thickness of the optical applicator. In some embodiments source emitters 21-24 are axially aligned in a parallel fashion and positioned at a predetermined spacing along the width of the optical applicator. Similarly, detector fibers 25-27 are axially aligned and positioned at a predetermined spacing along the width of the optical applicator. Detector fibers 25-27 can be any suitable type of device to detect the various parameters of the delivered therapy light 30 and can comprise point detectors configured to collect the therapy light and, in some embodiments, can comprise isotropic probe model IP85 available from Medlight S.A. Detector fibers 25-27 are optically coupled to a plurality of optical fibers and selectively optically coupled to a detector via an optical connector (53, FIG. 6).

Matrix material 28 is selected from a group of materials having a high scattering coefficient $\mu_s$ to effectively scatter the therapy light 30 and produce a highly uniform irradiance pattern 31 and a relatively low absorption coefficient $\mu_a$. In some embodiments of the present disclosure $\mu_s > 5$ cm$^{-1}$. The matrix material 28 of integrated optical applicator 2 is also selected from a group of materials having a mechanically flexibility which allows it to be bent and conform to different tissue surfaces. An important factor in the selection of matrix material 28 is its scattering coefficient and light transmissibility. Suitable embodiments of matrix material 28 includes a curable matrix material a suspension of polyvinyl chloride or other polymer particles in a liquid plasticizer, such as a plastisol base material and an engineering resin such as Elastic 50A available from Formlabs. The curable matrix materials can be cured using any known method including heat, chemical, light and other methods yielding a cured flexible matrix encapsulating the optical components in a fixed spatial position therein. In other embodiments, matrix material 28 can include known light scattering particles such as glass microspheres, metallic particles, saline and other substances that are known to have light scattering properties. In other embodiments, reflective coatings can be applied to some or all of the non-contact sides (top, and sides) integrated optical applicator 20 wherein all the light emitted by source emitters 21-24 would exit the optical applicator through the application side (bottom) 32. In some embodiments a reflective coating can be applied to all sides except for the application side to direct scattered light through the application side.

It should be recognized by those skilled in the art that position of the source emitters relative to target tissue 29 (Z direction), or so-called standoff position, is a predetermined distance from the bottom of the integrated optical applicator 20 and an important parameter to accurately control and maintain. Integrated optical applicator 20 can be custom made to provide a predetermined number and position of light diffusers and detector fibers within matrix 28. In practice a mold assembly can be provided having a cavity and suitable dimensions and features for producing the outside dimensions of integrated optical applicator 20. Source emitters and detector fibers can be spatially prepositioned within the mold and secured. Matrix material 28 can then be introduced to the mold encapsulating the light diffusers and detector fibers within the matrix. Once the matrix material has solidified, the spatial positions of the light diffusers and detector fibers is fixed within the optical applicator. Integrated optical applicator 20 can then be positioned over the target tissue of patient in an efficient and accurate manner.

Figure 4:
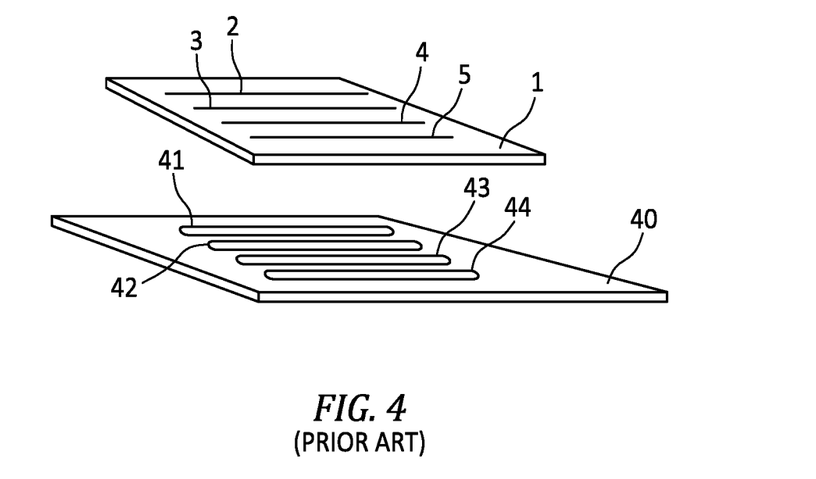
FIG. 4 is a schematic representation of a simulation of a light delivery device of the prior art.
Figure 5:
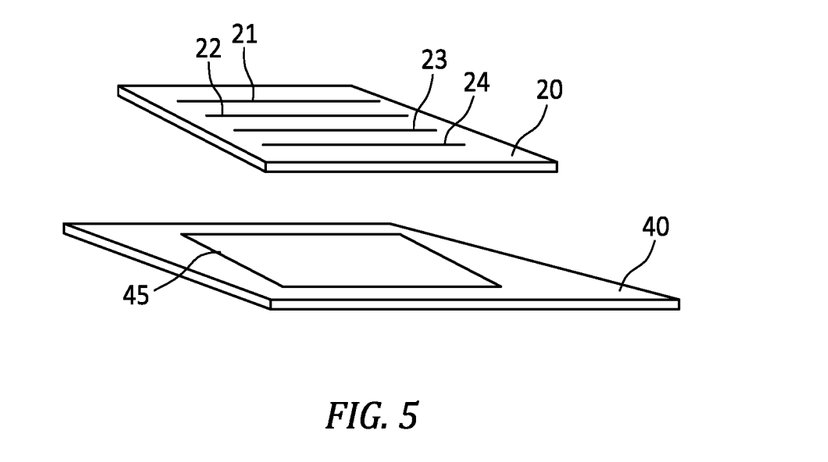
FIG. 5 is a schematic representation of a simulation of a light delivery device in accordance with the present disclosure.

The novel effect of integrated optical applicator can best be seen with reference to the simulations depicted in FIGS. 4 and 5. FIG. 4, from the prior art, shows applicator flap 1 of FIG. 1 with source emitters 2-5 positioned therein but without separate. The simulation includes a substrate 40 positioned below applicator flap 1. It is shown that source emitters 2-5 produce discrete respective irradiance patterns 41-44 with gaps positioned therebetween. In practice the gaps would mean that portions of targeted tissue would not receive therapy light and other portions may receive a larger dosage of therapy light than planned. In order to properly treat a targeted tissue area effectively the discrete respective irradiance patterns 41-44 would have to calculated ant the applicator would have to be moved to a second (or more) location during a procedure. Now with specific reference to FIG. 5, there is shown a simulation of integrated optical applicator 20 described herein above with reference to FIGS. 2, 3. In this simulation source emitters 21-24 are configured to transmit light from the light source at a predetermined wavelength (nm), and power level (W) to deliver a dosage of therapy light. The optical properties of integrated optical applicator 20 are configured to scatter the total available therapy light across a broader area than the source emitters alone. In this particular embodiment, irradiance pattern 45 covers a desired target area without gaps and with an accurate and predictable predetermined fluence ($J/cm^2$). This allows users of a PDT system including integrated optical applicator 20 to devise a planned therapy plan and carry it out with efficiency and accuracy.

Figure 6:
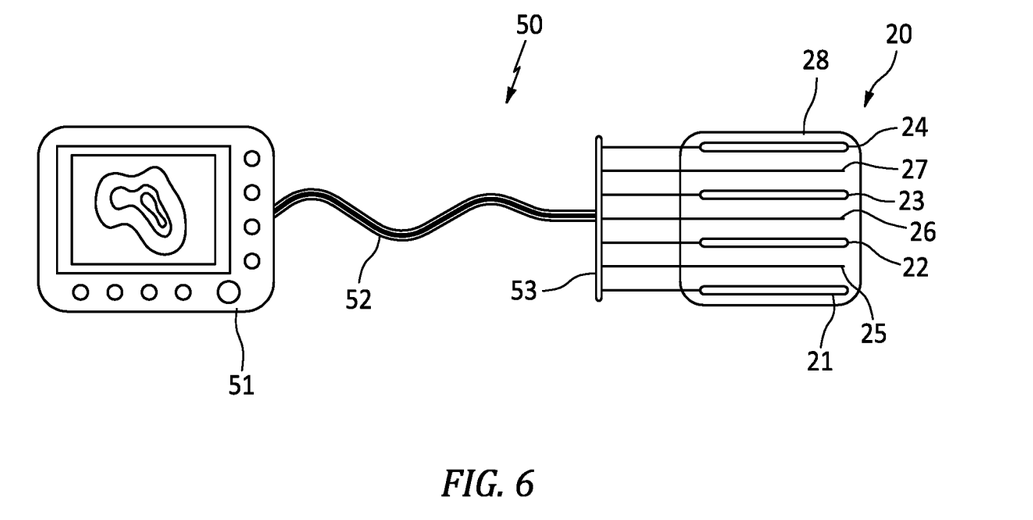
FIG. 6 is a schematic representation of a PDT system employing of a light delivery device in accordance with the present disclosure.

FIG. 6 shows a schematic of one embodiment of an optical light delivery system in the form of a PDT system 50 employing integrated optical applicator 20 for use in a photodynamic therapy procedure as will be disclosed in more detail herein after. The PDT system 50 is comprised of a number of components including an instrument 51, integrated optical applicator 20 and a optical tether 52 optically coupling the instrument to the integrated optical applicator via optical connector 53. Instrument 51 includes a light source, a spectrum analyzer, a microprocessor and an optional display. In PDT system 50, therapy light is provided by the source in instrument 51 and delivered to the tissue by source emitters 2-5 via integrated optical applicator 20 as disclosed herein before with reference to FIGS. 2, 3. The detector fibers 25-27 are distributed within integrated optical applicator 20 to detect therapy light emanating from source emitters 21-24. Optical tether 52 includes individual optical fibers sufficient in number to optically couple to a single one of the detector fibers 6-9 and source emitters 21-24 and can be connected by an optical connector 53. In operation, a medical professional can obtain a digital file (x-ray, MRI, CAT scan, etc.) of a position of an abnormal tissue area to be treated using a PDT procedure. The digital file should contain at least X and Y coordinates of the area relative to a position in space. A patient is administered a photosensitizing drug and is prepared for the surgical treatment. An integrated optical applicator is prepared with a proper fluence disclosed herein above to produce a target irradiance pattern that closely matches the abnormal tissue area to be treated using a PDT procedure. A treatment plan is devised by medical personnel based on, among other things the type of therapy, the source, the fluence of integrated optical applicator 20, a dosage therapy light amount and the specific photosensitizing drug, wherein the treatment plan is directed at treating the abnormal tissue in the target area. The integrated optical applicator is positioned on top of the abnormal tissue area to be treated using a PDT procedure with the application side positioned in direct contact with the tissue. The integrated optical applicator is positioned using the X and Y coordinates of the digital file and a digital file of the target irradiance pattern at the predetermined standoff position from the tissue. Instrument 51 is powered on and therapy light is delivered to source emitters 21-24 via optical tether 52, the therapy light is scattered by matrix 28 and applied to the target area through application side 32 of integrated optical applicator 20. The amount of therapy light is collected by detector fibers 25-27 and is sent back to instrument 51 via optical tether 52 wherein a dosage therapy light amount is calculated on a cumulative basis. The procedure is continued until the dosage therapy light amount is substantially equal to the treatment plan. In some embodiments, the treatment plan can be updated based on the original treatment plan and calculations made by the microprocessor based on feedback from the therapy light collected by the detector fibers 25-27.

All of the methods disclosed and claimed herein can be made and executed without undue experimentation in light of the present disclosure. While the apparatus and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention.

Although the invention(s) is/are described herein with reference to specific embodiments, various modifications and changes can be made without departing from the scope of the present disclosure, as presently set forth in the claims below. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms scatter, diffuse and spread are among the same terms that similar meaning as delivering total available therapy light to a broader area than that of prior art methods. The terms "a" and "an" are defined as one or more unless stated otherwise the terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

While the foregoing is directed to embodiments of the present disclosure, other and further embodiments of the disclosure may be devised without departing from the basic scope thereof, and the scope thereof is determined by the claims that follow.

What is claimed is:

1. An optical light delivery device comprising:
a plurality of source emitting devices configured to be optically coupled to a source wherein the source is configured to produce a therapy light and wherein the plurality of source emitting devices are further configured to transmit the therapy light;
a flexible matrix comprising a material selected from a group of materials having a scattering coefficient greater than 5 cm$^{-1}$ encapsulating and spatially fixing the plurality of source emitting devices therein parallel to each other;
the flexible matrix configured to scatter a light emitted from at least one of the plurality of source emitting devices; and
at least one detector fiber encapsulated and spatially fixed within the flexible matrix parallel and proximate to the plurality of source emitting devices, the at least one detector fiber configured to detect a light emitted from at least one of the plurality of source emitting devices and configured to be coupled to a detector.

2. The optical light delivery device of claim 1 wherein the plurality of source emitting devices are spatially fixed at a predetermined standoff position from an application side of the optical light delivery device.

3. The optical light delivery device of claim 2 wherein the plurality of source emitting devices are axially aligned and spatially fixed at a first predetermined spacing along a width of the flexible matrix and wherein the at least one detector fiber comprises a plurality of detector fibers that are axially aligned and spatially fixed at a second predetermined spacing along the width of the flexible matrix.

4. The optical light delivery device of claim 3 wherein the plurality of detector fibers are optically coupled to a plurality of optical fibers.

5. The optical light delivery device of claim 4 wherein the plurality of detector fibers comprise a plurality of isotropic probes.

6. The optical light delivery device of claim 2 is further configured to produce a predetermined fluence at the application side.

7. The optical light delivery device of claim 1 wherein the plurality of source emitting devices comprise a plurality of cylindrical light diffusers and wherein the plurality of cylindrical light diffusers are optically coupled to a plurality of optical fibers and configured to transmit the therapy light.

8. An optical light delivery system comprising:
a therapy light source; and
an integrated optical applicator comprising:
a plurality of source emitting devices optically coupled to the therapy light source spatially fixed at a predetermined standoff position from an application side of the integrated optical applicator;
a flexible matrix encapsulating and spatially fixing the plurality of source emitting devices therein;
a plurality of detector fibers comprising a plurality of isotropic probes encapsulated and spatially fixed within the flexible matrix proximate the plurality of source emitting devices, the plurality of detector fibers optically coupled to a detector and configured to detect a therapy light emitted from at least one of the plurality of source emitting devices;
the flexible matrix is comprised of a light scattering material and is configured to scatter a therapy light emitted from at least one of the plurality of source emitting devices;
wherein the plurality of source emitting devices are axially aligned and spatially fixed at a first predetermined spacing along a width of the flexible matrix and wherein the plurality of detector fibers are axially aligned and spatially fixed at a second predetermined spacing along the width of the flexible matrix;
wherein the plurality of source emitting devices comprise a plurality of cylindrical light diffusers and wherein the plurality of cylindrical light diffusers are optically coupled to an optical connector and wherein the plurality of detector fibers are optically coupled to the optical connector; and
an optical tether optically coupled to the optical connector and the therapy light source.

9. The optical light delivery system of claim 8 wherein the integrated optical applicator is configured to produce a uniform irradiance pattern.

10. The optical light delivery system of claim 9 wherein the flexible matrix is selected from a group of materials having a scattering coefficient greater than 5 cm$^{-1}$.

11. The optical light delivery system of claim 10 wherein the integrated optical applicator is configured to produce a predetermined fluence at an application side.

12. A method of manufacturing an integrated optical applicator comprising:
providing a mold assembly defining a cavity having a bottom, a length and a width;
positioning a plurality of cylindrical light diffusers in the mold assembly axially aligned along the length and parallel to each other, at a predetermined spacing along the width and at a predetermined distance from the bottom;
positioning a plurality of detector fibers in the mold assembly parallel and proximate to the plurality of cylindrical light diffusers;
dispensing a curable matrix material in the cavity and encapsulating the plurality of cylindrical light diffusers and the plurality of detector fibers therein; and
curing the curable matrix material into a flexible matrix and spatially fixing the plurality of cylindrical light diffusers and the plurality of detector fibers therein; and
wherein the curable matrix material is comprised of a light scattering material having a scattering coefficient greater than 5 cm$^{-1}$.

13. The method of manufacturing an integrated optical applicator of claim 12 wherein the light scattering material further includes light scattering particles including any of glass microspheres, metallic particles and saline.

14. The method of manufacturing an integrated optical applicator of claim 12 wherein a portion of the flexible matrix positioned against the bottom during the curing produces an application side of the integrated optical applicator and the predetermined distance from the bottom produces a standoff position of the plurality of cylindrical light diffusers from the application side.

15. The method of manufacturing an integrated optical applicator of claim 14 where a reflective coating is applied to any of a surface of the integrated optical applicator except for the application side.

16. A method of performing a photodynamic therapy procedure comprising
providing a therapy light source;
providing an integrated optical applicator comprising:
a plurality of source emitting devices positioned parallel to each other;
a flexible matrix encapsulating and spatially fixing the plurality of source emitting devices therein; and the flexible matrix is comprised of a light scattering material and is configured to scatter a therapy light emitted from at least one of the plurality of source emitting devices;

optically coupling the plurality of source emitting devices to the therapy light source;

providing a photosensitizing drug to a tissue of a patient;

positioning an application side of the integrated optical applicator against a target area of the tissue;

delivering a therapy light from at least one of the plurality of source emitting devices to at least a portion of the target area;

producing an irradiance pattern to the at least a portion of the target area; and obtaining a digital file of the target area including a position of the target area; and wherein the positioning of the application side of the integrated optical applicator against the target area of the tissue is based on the digital file.

17. The method of performing a photodynamic therapy procedure of claim 16 further comprising a treatment plan; the integrated optical applicator further comprising spatial fixing a plurality of detector fibers proximate the plurality of source emitting devices and optically coupling the plurality of detector fibers to a detector;

providing a microprocessor electronically coupled to the detector and the therapy light source;

detecting the therapy light with the at least one of the plurality of detector fibers and, using the microprocessor, producing a dosage therapy light amount; and comparing, using the microprocessor, the dosage therapy light amount with the treatment plan.

18. The method of performing a photodynamic therapy procedure of claim 17 further comprising continuing to delivering the therapy light and detecting the therapy light until the dosage therapy light amount is substantially equal to the treatment plan.

19. The method of performing a photodynamic therapy procedure of claim 16 wherein producing the irradiance pattern to the at least a portion of the target area comprises producing a substantially equal fluence across the at least a portion of the target area.

20. The method of performing a photodynamic therapy procedure of claim 17 wherein producing a dosage therapy light amount is performed on a cumulative basis during the photodynamic therapy procedure.

* * * * *